(12) United States Patent
Abraham et al.

(10) Patent No.: US 8,462,765 B2
(45) Date of Patent: Jun. 11, 2013

(54) METHOD AND APPARATUS TO PERFORM RANGING OPERATIONS FOR WIRELESS STATIONS

(75) Inventors: Santosh P. Abraham, San Diego, CA (US); Sameer Vermani, San Diego, CA (US); Hemanth Sampath, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 606 days.

(21) Appl. No.: 12/543,304

(22) Filed: Aug. 18, 2009

(65) Prior Publication Data
US 2010/0046492 A1 Feb. 25, 2010

Related U.S. Application Data

(60) Provisional application No. 61/090,438, filed on Aug. 20, 2008.

(51) Int. Cl.
H04B 7/216 (2006.01)
H04J 3/06 (2006.01)
H04L 7/00 (2006.01)

(52) U.S. Cl.
USPC ........... 370/350; 370/503; 370/509; 455/503; 375/356

(58) Field of Classification Search
USPC ................. 370/312, 432, 350, 503, 507, 509, 370/512; 375/356, 358; 455/502, 503
See application file for complete search history.

(56) References Cited

U.S. PATENT DOCUMENTS

| | | | | |
|---|---|---|---|---|
| 6,671,260 | B1* | 12/2003 | Engstrand | 370/238 |
| 6,956,865 | B1* | 10/2005 | Khaunte et al. | 370/442 |
| 7,352,718 | B1* | 4/2008 | Perahia et al. | 370/329 |
| 7,596,113 | B1* | 9/2009 | Kingston et al. | 370/320 |
| 7,688,747 | B2 | 3/2010 | Zumsteg | |
| 7,995,525 | B1* | 8/2011 | Perahia et al. | 370/329 |
| 2002/0181492 | A1* | 12/2002 | Kasami et al. | 370/445 |
| 2003/0039273 | A1 | 2/2003 | Jang | |
| 2005/0041573 | A1* | 2/2005 | Eom et al. | 370/208 |
| 2005/0136910 | A1* | 6/2005 | Li et al. | 455/423 |
| 2006/0154684 | A1* | 7/2006 | Meiyappan | 455/522 |

(Continued)

FOREIGN PATENT DOCUMENTS

| | | |
|---|---|---|
| EP | 1286505 A1 | 2/2003 |
| EP | 1944993 | 7/2008 |

(Continued)

OTHER PUBLICATIONS

International Search Report—PCT/US2009/054491—International Search Authority, European Patent Office, Feb. 12, 2009.

(Continued)

Primary Examiner — Chi Pham
Assistant Examiner — Ahmed Elallam
(74) Attorney, Agent, or Firm — Kevin Cheatham

(57) ABSTRACT

Certain embodiments provide methods and apparatus for adjusting timing in an SDMA system. One method for adjusting the timing of packet transmissions in a wireless communications system, that may be performed by an access point, includes receiving ranging signals from a plurality of wireless network nodes, determining timing adjustment information for adjusting starting timing of packet transmissions from the wireless network nodes based on the ranging signals, and communicating the timing adjustment information to the wireless network nodes.

35 Claims, 8 Drawing Sheets

U.S. PATENT DOCUMENTS

| | | | |
|---|---|---|---|
| 2007/0064740 A1* | 3/2007 | Waxman | 370/498 |
| 2007/0202882 A1 | 8/2007 | Ju et al. | |
| 2007/0293214 A1* | 12/2007 | Ansari et al. | 455/427 |
| 2008/0159427 A1* | 7/2008 | Kang et al. | 375/260 |
| 2010/0009707 A1* | 1/2010 | Porat | 455/517 |
| 2010/0142441 A1 | 6/2010 | Toda et al. | |

FOREIGN PATENT DOCUMENTS

| | | |
|---|---|---|
| JP | 2003110583 A | 4/2003 |
| JP | 2008042861 A | 2/2008 |
| JP | 2008113252 A | 5/2008 |
| JP | 2010500788 A | 1/2010 |
| KR | 20070119474 A | 12/2007 |
| WO | WO2007145419 | 12/2007 |

OTHER PUBLICATIONS

Written Opinion—PCT/US2009/054491—International Search Authority European Patent Office—Dec. 2, 2009.

Taiwan Search Report—TW098128139—TIPO—Sep. 18, 2012.

* cited by examiner

METHOD AND APPARATUS TO PERFORM RANGING OPERATIONS FOR WIRELESS STATIONS

CROSS-REFERENCE TO RELATED APPLICATION

This application claims benefit of U.S. Provisional Patent Application Ser. No. 61/090,438 filed Aug. 20, 2008, which is herein incorporated by reference in its entirety.

BACKGROUND

In order to address the issue of increasing bandwidth requirements that are demanded for wireless communications systems, different schemes are being developed to allow multiple user terminals to communicate with a single base station by sharing the same channel (same time and frequency resources) while achieving high data throughputs. Spatial Division Multiple Access (SDMA) represents one such approach that has recently emerged as a popular technique for the next generation communication systems. SDMA technique has been adopted in several emerging wireless communications standards such as IEEE 802.11 (IEEE is the acronym for the Institute of Electrical and Electronic Engineers, 3 Park Avenue, 17th floor, New York, N.Y.) and the 3rd Generation Partnership Project (3GPP).

In SDMA systems, a base station may transmit or receive different signals to or from a plurality of mobile user terminals at the same time and using the same frequency. In order to achieve reliable data communication, user terminals may need to be located in sufficiently different directions. Independent signals may be simultaneously transmitted from each of a plurality of space-separated antennas at the base station. Consequently, the combined transmissions may be directional, i.e., the signal that is dedicated for each user terminal may be relatively strong in the direction of that particular user terminal and sufficiently weak in directions of other user terminals. Similarly, the base station may simultaneously receive on the same frequency the combined signals from multiple user terminals through each of the antennas separated in space, and the combined received signals from multiple antennas may be split into independent signals transmitted from each user terminal by applying the appropriate signal processing technique.

A multiple-input multiple-output (MIMO) wireless system employs multiple ($N_T$) transmit antennas and multiple ($N_R$) receive antennas for data transmission. A MIMO channel formed by the $N_T$ transmit and $N_R$ receive antennas may be decomposed into $N_S$ spatial channels, where $N_S \leq \min\{N_T, N_R\}$. The $N_S$ spatial channels may be used to transmit $N_S$ independent data streams to achieve greater overall throughput.

In a multiple-access MIMO system based on SDMA, an access point can communicate with one or more user terminals at any given moment. If the access point communicates with a single user terminal, then the $N_T$ transmit antennas are associated with one transmitting entity (e.g., either the access point or the user terminal), and the $N_R$ receive antennas are associated with one receiving entity (e.g., either the user terminal or the access point). The access point can also communicate with multiple user terminals simultaneously via SDMA. For SDMA, the access point utilizes multiple antennas for data transmission and reception, and each of the user terminals typically utilizes one antenna for data transmission and multiple antennas for data reception.

SUMMARY

Certain embodiments provide a method for adjusting the timing of packet transmissions in a wireless communications system. The method generally includes receiving ranging signals from a plurality of wireless network nodes, determining timing adjustment information for adjusting starting timing of packet transmissions from the wireless network nodes based on the ranging signals, and communicating the timing adjustment information to the wireless network nodes.

Certain embodiments provide a method for adjusting the timing of packet transmissions in a wireless communications system. The method generally includes receiving timing adjustment information and utilizing the timing adjustment information to adjust the timing of transmitting packets on an uplink connection used by multiple wireless nodes to simultaneously transmit packets via a multiple access (MA) scheme.

Certain embodiments provide an apparatus for adjusting the timing of packet transmissions in a wireless communications system. The apparatus generally includes logic for receiving ranging signals from a plurality of wireless network nodes, logic for determining timing adjustment information for adjusting starting timing of packet transmissions from the wireless network nodes based on the ranging signals, and logic for communicating the timing adjustment information to the wireless network nodes.

Certain embodiments provide an apparatus for adjusting the timing of packet transmissions in a wireless communications system. The apparatus generally includes logic for receiving timing adjustment information and logic for utilizing the timing adjustment information to adjust the timing of transmitting packets on an uplink connection used by multiple wireless nodes to simultaneously transmit packets via a multiple access (MA) scheme.

Certain embodiments provide an apparatus for adjusting the timing of packet transmissions in a wireless communications system. The apparatus generally includes means for receiving ranging signals from a plurality of wireless network nodes, means for determining timing adjustment information for adjusting starting timing of packet transmissions from the wireless network nodes based on the ranging signals, and means for communicating the timing adjustment information to the wireless network nodes.

Certain embodiments provide an apparatus for adjusting the timing of packet transmissions in a wireless communications system. The apparatus generally includes means for receiving timing adjustment information and means for utilizing the timing adjustment information to adjust the timing of transmitting packets on an uplink connection used by multiple wireless nodes to simultaneously transmit packets via a multiple access (MA) scheme.

Certain embodiments provide a computer-program product for adjusting the timing of packet transmissions in a wireless communications system comprising a computer readable medium having instructions stored thereon, the instructions being executable by one or more processors. The instructions generally include instructions for receiving ranging signals from a plurality of wireless network nodes, determining timing adjustment information for adjusting starting timing of packet transmissions from the wireless network nodes based on the ranging signals, and communicating the timing adjustment information to the wireless network nodes.

Certain embodiments provide a computer-program product for adjusting the timing of packet transmissions in a wireless communications system comprising a computer readable medium having instructions stored thereon, the instructions being executable by one or more processors. The instructions generally include instructions for receiving timing adjustment information and utilizing the timing adjustment information to adjust the timing of transmitting packets on an uplink connection used by multiple wireless nodes to simultaneously transmit packets via a multiple access (MA) scheme.

BRIEF DESCRIPTION OF THE DRAWINGS

So that the manner in which the above recited features of the present disclosure can be understood in detail, a more particular description, briefly summarized above, may be had by reference to embodiments, some of which are illustrated in the appended drawings. It is to be noted, however, that the appended drawings illustrate only certain typical embodiments of this disclosure and are therefore not to be considered limiting of its scope, for the description may admit to other equally effective embodiments.

DETAILED DESCRIPTION

The word "exemplary" is used herein to mean "serving as an example, instance, or illustration." Any embodiment described herein as "exemplary" is not necessarily to be construed as preferred or advantageous over other embodiments.

The multi-antenna transmission techniques described herein may be used in combination with various wireless technologies such as Code Division Multiple Access (CDMA), Orthogonal Frequency Division Multiplexing (OFDM), Time Division Multiple Access (TDMA), and so on. Multiple user terminals can concurrently transmit/receive data via different (1) orthogonal code channels for CDMA, (2) time slots for TDMA, or (3) subbands for OFDM. A CDMA system may implement IS-2000, IS-95, IS-856, Wideband-CDMA (W-CDMA), or some other standards. An OFDM system may implement IEEE 802.11 or some other standards. A TDMA system may implement GSM or some other standards. These various standards are known in the art.

Figure 1:
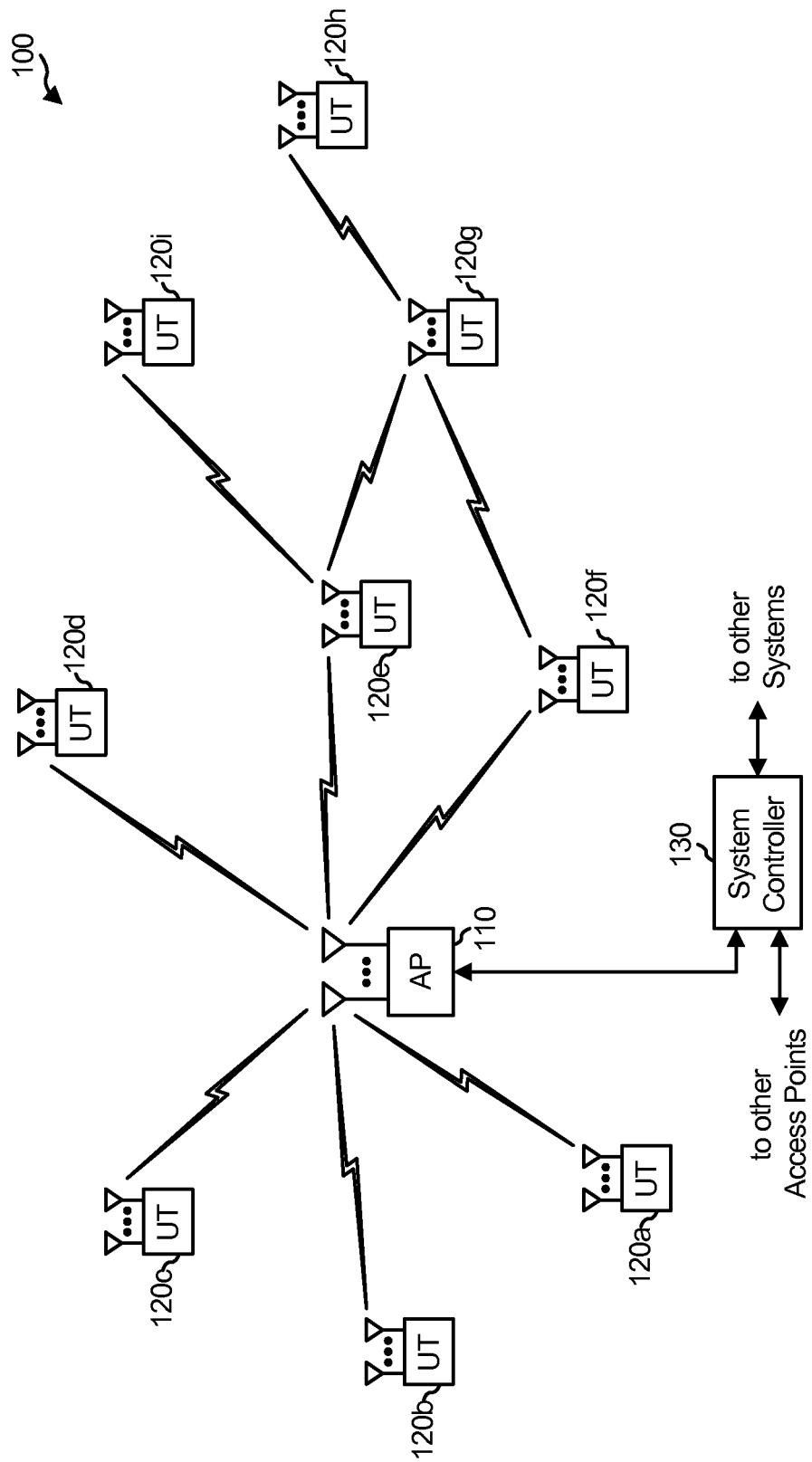
FIG. 1 shows a spatial division multiple access MIMO wireless system in accordance with certain embodiments of the present disclosure.

FIG. 1 shows a multiple-access MIMO system 100 with access points and user terminals. For simplicity, only one access point 110 is shown in FIG. 1. An access point is generally a fixed station that communicates with the user terminals and may also be referred to as a base station or some other terminology. A user terminal may be fixed or mobile and may also be referred to as a mobile station, a wireless device or some other terminology. Access point 110 may communicate with one or more user terminals 120 at any given moment on the downlink and uplink. The downlink (i.e., forward link) is the communication link from the access point to the user terminals, and the uplink (i.e., reverse link) is the communication link from the user terminals to the access point. A user terminal may also communicate peer-to-peer with another user terminal. A system controller 130 couples to and provides coordination and control for the access points.

While portions of the following disclosure will describe user terminals 120 capable of communicating via SDMA, for certain embodiments, the user terminals 120 may also include some user terminals that do not support SDMA. Thus, for such embodiments, an AP 110 may be configured to communicate with both SDMA and non-SDMA user terminals. This approach may conveniently allow older versions of user terminals ("legacy" stations) to remain deployed in an enterprise, extending their useful lifetime, while allowing newer SDMA user terminals to be introduced as deemed appropriate.

System 100 employs multiple transmit and multiple receive antennas for data transmission on the downlink and uplink. Access point 110 is equipped with $N_{ap}$ antennas and represents the multiple-input (MI) for downlink transmissions and the multiple-output (MO) for uplink transmissions. A set of $N_u$ selected user terminals 120 collectively represents the multiple-output for downlink transmissions and the multiple-input for uplink transmissions. For pure SDMA, it is desired to have $N_{ap} \geq N_u \geq 1$ if the data symbol streams for the $N_u$ user terminals are not multiplexed in code, frequency or time by some means. $N_u$ may be greater than Nap if the data symbol streams can be multiplexed using different code channels with CDMA, disjoint sets of subbands with OFDM, and so on. Each selected user terminal transmits user-specific data to and/or receives user-specific data from the access point. In general, each selected user terminal may be equipped with one or multiple antennas (i.e., $N_{ut} \geq 1$). The $N_u$ selected user terminals can have the same or different number of antennas.

SDMA system 100 may be a time division duplex (TDD) system or a frequency division duplex (FDD) system. For a TDD system, the downlink and uplink share the same frequency band. For an FDD system, the downlink and uplink use different frequency bands. MIMO system 100 may also utilize a single carrier or multiple carriers for transmission. Each user terminal may be equipped with a single antenna (e.g., in order to keep costs down) or multiple antennas (e.g., where the additional cost can be supported).

Figure 2:
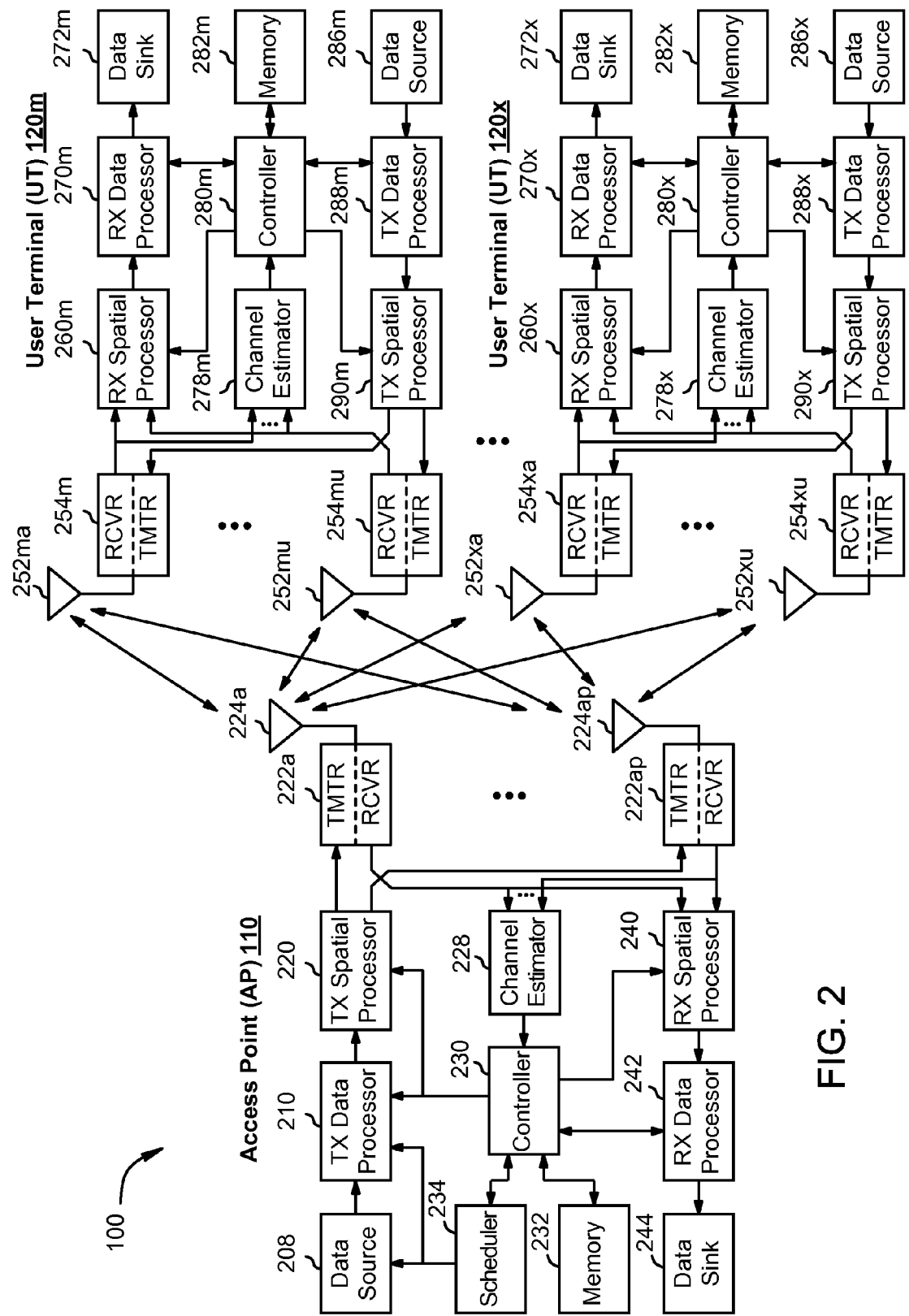
FIG. 2 shows a block diagram of an access point and two user terminals in accordance with certain embodiments of the present disclosure.

FIG. 2 shows a block diagram of access point 110 and two user terminals 120m and 120x in MIMO system 100. Access point 110 is equipped with $N_{ap}$ antennas 224a through 224ap. User terminal 120m is equipped with $N_{ut,m}$ antennas 252ma through 252m,u, and user terminal 120x is equipped with $N_{ut,x}$ antennas 252xa through 252xu. Access point 110 is a transmitting entity for the downlink and a receiving entity for the uplink. Each user terminal 120 is a transmitting entity for the uplink and a receiving entity for the downlink. As used herein, a "transmitting entity" is an independently operated apparatus or device capable of transmitting data via a wireless channel, and a "receiving entity" is an independently operated apparatus or device capable of receiving data via a wireless channel. In the following description, the subscript "dn" denotes the downlink, the subscript "up" denotes the uplink, $N_{up}$ user terminals are selected for simultaneous transmission on the uplink, $N_{dn}$ user terminals are selected for simultaneous transmission on the downlink, $N_{up}$ may or may not be equal to $N_{dn}$, and $N_{up}$ and $N_{dn}$ may be static values or can change for each scheduling interval. The beam-steering or some other spatial processing technique may be used at the access point and user terminal.

On the uplink, at each user terminal 120 selected for uplink transmission, a TX data processor 288 receives traffic data from a data source 286 and control data from a controller 280. TX data processor 288 processes (e.g., encodes, interleaves, and modulates) the traffic data $\{d_{up,m}\}$ for the user terminal based on the coding and modulation schemes associated with the rate selected for the user terminal and provides a data symbol stream $\{s_{up,m}\}$. A TX spatial processor 290 performs spatial processing on the data symbol stream $\{s_{up,m}\}$ and provides $N_{ut,m}$ transmit symbol streams for the $N_{ut,m}$ antennas. Each transmitter unit (TMTR) 254 receives and processes (e.g., converts to analog, amplifies, filters, and frequency upconverts) a respective transmit symbol stream to generate an uplink signal. $N_{ut,m}$ transmitter units 254 provide $N_{ut,m}$ uplink signals for transmission from $N_{ut,m}$ antennas 252 to the access point.

$N_{up}$ user terminals may be scheduled for simultaneous transmission on the uplink. Each of these user terminals performs spatial processing on its data symbol stream and transmits its set of transmit symbol streams on the uplink to the access point.

At access point 110, Nap antennas 224a through 224ap receive the uplink signals from all $N_{up}$ user terminals transmitting on the uplink. Each antenna 224 provides a received signal to a respective receiver unit (RCVR) 222. Each receiver unit 222 performs processing complementary to that performed by transmitter unit 254 and provides a received symbol stream. An RX spatial processor 240 performs receiver spatial processing on the $N_{ap}$ received symbol streams from $N_{ap}$ receiver units 222 and provides $N_{up}$ recovered uplink data symbol streams. The receiver spatial processing is performed in accordance with the channel correlation matrix inversion (CCMI), minimum mean square error (MMSE), soft interference cancellation (SIC), or some other technique. Each recovered uplink data symbol stream $\{s_{up,m}\}$ is an estimate of a data symbol stream $\{s_{up,m}\}$ transmitted by a respective user terminal. An RX data processor 242 processes (e.g., demodulates, deinterleaves, and decodes) each recovered uplink data symbol stream {sp,m} in accordance with the rate used for that stream to obtain decoded data. The decoded data for each user terminal may be provided to a data sink 244 for storage and/or a controller 230 for further processing.

On the downlink, at access point 110, a TX data processor 210 receives traffic data from a data source 208 for $N_d$, user terminals scheduled for downlink transmission, control data from a controller 230, and possibly other data from a scheduler 234. The various types of data may be sent on different transport channels. TX data processor 210 processes (e.g., encodes, interleaves, and modulates) the traffic data for each user terminal based on the rate selected for that user terminal. TX data processor 210 provides $N_{dn}$ downlink data symbol streams for the $N_{dn}$ user terminals. A TX spatial processor 220 performs spatial processing on the $N_{dn}$ downlink data symbol streams, and provides $N_{ap}$ transmit symbol streams for the $N_{ap}$ antennas. Each transmitter unit 222 receives and processes a respective transmit symbol stream to generate a downlink signal. $N_{ap}$ transmitter units 222 providing $N_{ap}$ downlink signals for transmission from $N_{ap}$ antennas 224 to the user terminals.

At each user terminal 120, $N_{ut,m}$ antennas 252 receive the $N_{ap}$ downlink signals from access point 110. Each receiver unit 254 processes a received signal from an associated antenna 252 and provides a received symbol stream. An RX spatial processor 260 performs receiver spatial processing on $N_{ut,m}$ received symbol streams from $N_{ut,m}$ receiver units 254 and provides a recovered downlink data symbol stream $\{s_{dn,m}\}$ for the user terminal. The receiver spatial processing is performed in accordance with the CCMI, MMSE or some other technique. An RX data processor 270 processes (e.g., demodulates, deinterleaves and decodes) the recovered downlink data symbol stream to obtain decoded data for the user terminal.

At each user terminal 120, a channel estimator 278 estimates the downlink channel response and provides downlink channel estimates, which may include channel gain estimates, $SN_R$ estimates, and so on. Similarly, a channel estimator 228 estimates the uplink channel response and provides uplink channel estimates. Controller 280 for each user terminal typically derives the spatial filter matrix for the user terminal based on the downlink channel response matrix $H_{dn,m}$ for that user terminal. Controller 230 derives the spatial filter matrix for the access point based on the effective uplink channel response matrix $H_{up,eff}$. Controller 280 for each user terminal may send feedback information (e.g., the downlink and/or uplink steering vectors, SNR estimates, and so on) to the access point. Controllers 230 and 280 also control the operation of various processing units at access point 110 and user terminal 120, respectively.

Figure 3:
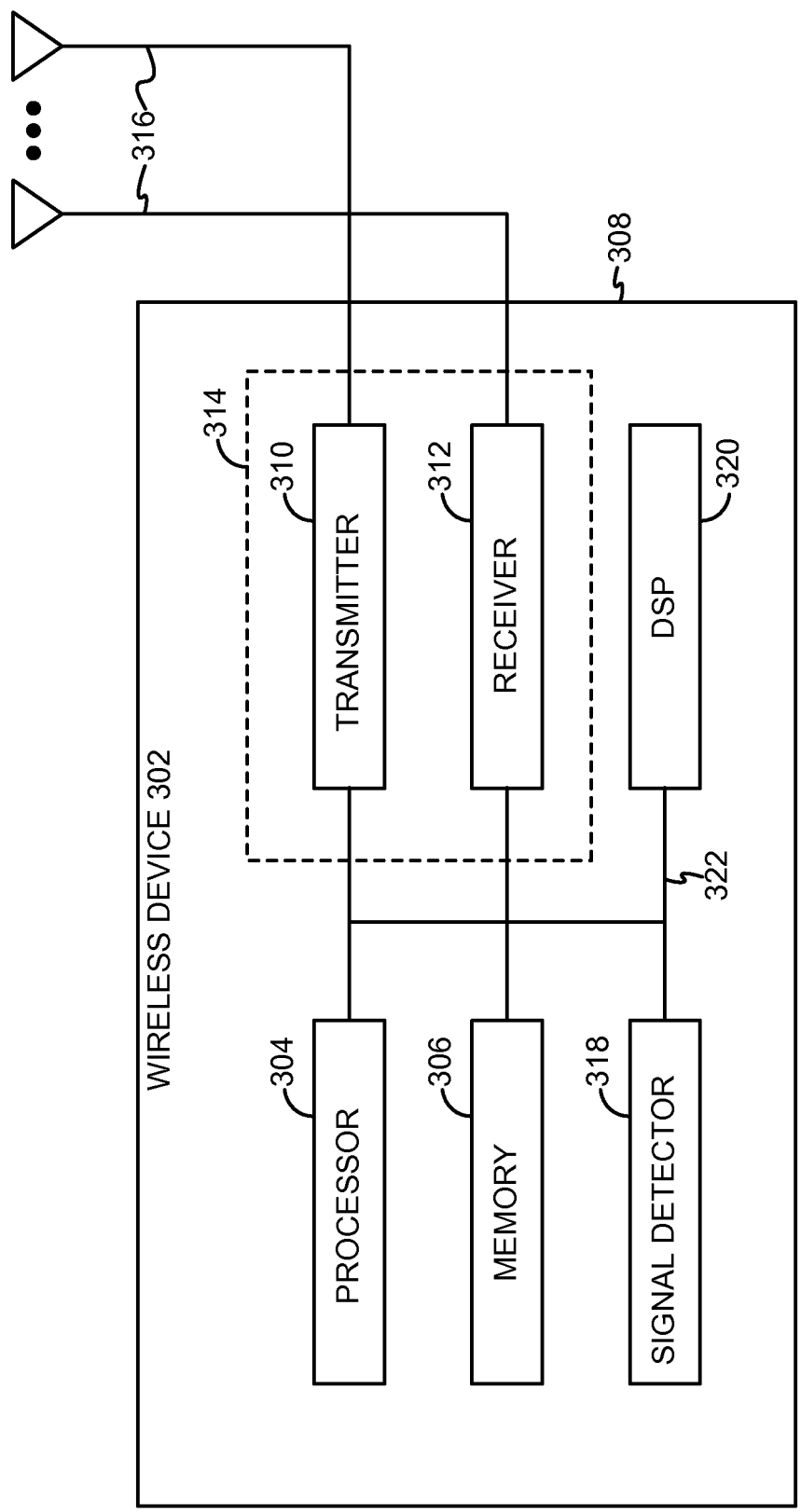
FIG. 3 illustrates example components of a wireless device, in accordance with certain embodiments of the present disclosure.

FIG. 3 illustrates various components that may be utilized in a wireless device 302 that may be employed within the system 100. The wireless device 302 is an example of a device that may be configured to implement the various methods described herein. The wireless device 302 may be an access point 110 or a user terminal 120.

The wireless device 302 may include a processor 304 which controls operation of the wireless device 302. The processor 304 may also be referred to as a central processing unit (CPU). Memory 306, which may include both read-only memory (ROM) and random access memory (RAM), provides instructions and data to the processor 304. A portion of the memory 306 may also include non-volatile random access memory (NVRAM). The processor 304 typically performs logical and arithmetic operations based on program instructions stored within the memory 306. The instructions in the memory 306 may be executable to implement the methods described herein.

The wireless device 302 may also include a housing 308 that may include a transmitter 310 and a receiver 312 to allow transmission and reception of data between the wireless device 302 and a remote location. The transmitter 310 and receiver 312 may be combined into a transceiver 314. A plurality of transmit antennas 316 may be attached to the housing 308 and electrically coupled to the transceiver 314. The wireless device 302 may also include (not shown) multiple transmitters, multiple receivers, and multiple transceivers.

The wireless device 302 may also include a signal detector 318 that may be used in an effort to detect and quantify the level of signals received by the transceiver 314. The signal detector 318 may detect such signals as total energy, energy per subcarrier per symbol, power spectral density and other signals. The wireless device 302 may also include a digital signal processor (DSP) 320 for use in processing signals.

The various components of the wireless device 302 may be coupled together by a bus system 322, which may include a power bus, a control signal bus, and a status signal bus in addition to a data bus.

As used herein, the term "legacy" generally refers to wireless network nodes that support 802.11n or earlier versions of the 802.11 standard.

While certain techniques are described herein with reference to SDMA, those skilled in the art will recognize the techniques may be generally applied in systems utilizing any type of multiple access schemes, such as SDMA, OFDMA, CDMA, and combinations thereof.

Ranging Protocol for SDMA Transmission in WLANS

In wireless local area network (WLAN) systems, SDMA transmissions from multiple stations are required to be time synchronized to a fraction of a cyclic prefix in order to have accurate decoding. Embodiments of the present disclosure provide a ranging protocol for synchronizing SDMA transmissions in a WLAN.

Figure 4:
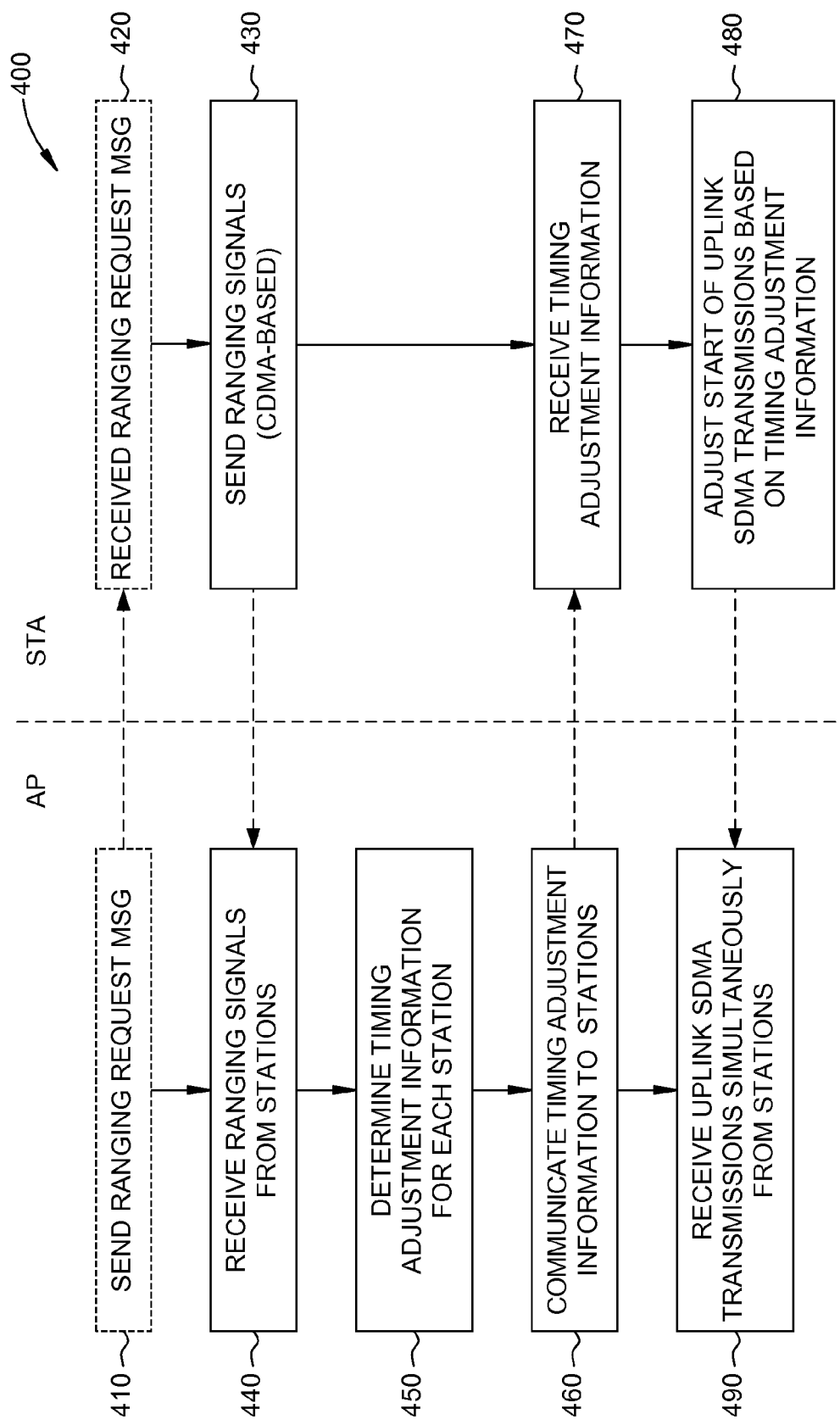
FIG. 4 is a flow diagram illustrating a method for synchronizing a WLAN using ranging signals, according to one embodiment of the disclosure.

FIG. 4 illustrates example operations for ranging that may be performed in order to synchronize a WLAN using ranging signals, according to one embodiment of the disclosure. The operations include operations performed by the AP and corresponding operations performed by the station. As will be described in greater detail below, in an SDMA system, multiple stations may perform the illustrated operations simultaneously.

The operations begin, at 410, with an access point (AP) sending a ranging request message to a plurality of stations (STAs). At 420, the station receives the ranging request and, in response, sends ranging signals, at 430. At 440, the AP receives the ranging signals and determines timing adjustment information for each station, at 450.

For certain embodiments, operations 410 and 420 may not be necessary. For example, rather than send ranging signals in response to a ranging request, stations may send ranging signals according to some other mechanism. As long as the AP has a timing reference allowing it to determine when the ranging signals were sent, the AP could still determine propagation delay for each station. Further, for certain embodiments, the AP may be able to determine timing adjustments based on some mechanism other than ranging signals, such as some other time synchronized signals that allow it to determine a propagation delay.

In any case, at 460, the AP communicates timing adjustment information to the stations. At 470, the station receives the timing adjustment information. At 480, the station adjusts the start time of uplink transmissions based on the timing adjustment information. The adjustments made at each station, ideally, result in the UL transmissions arriving at the AP time aligned within an acceptable tolerance. At 490, the AP receives the uplink SDMA packets.

Figure 5:
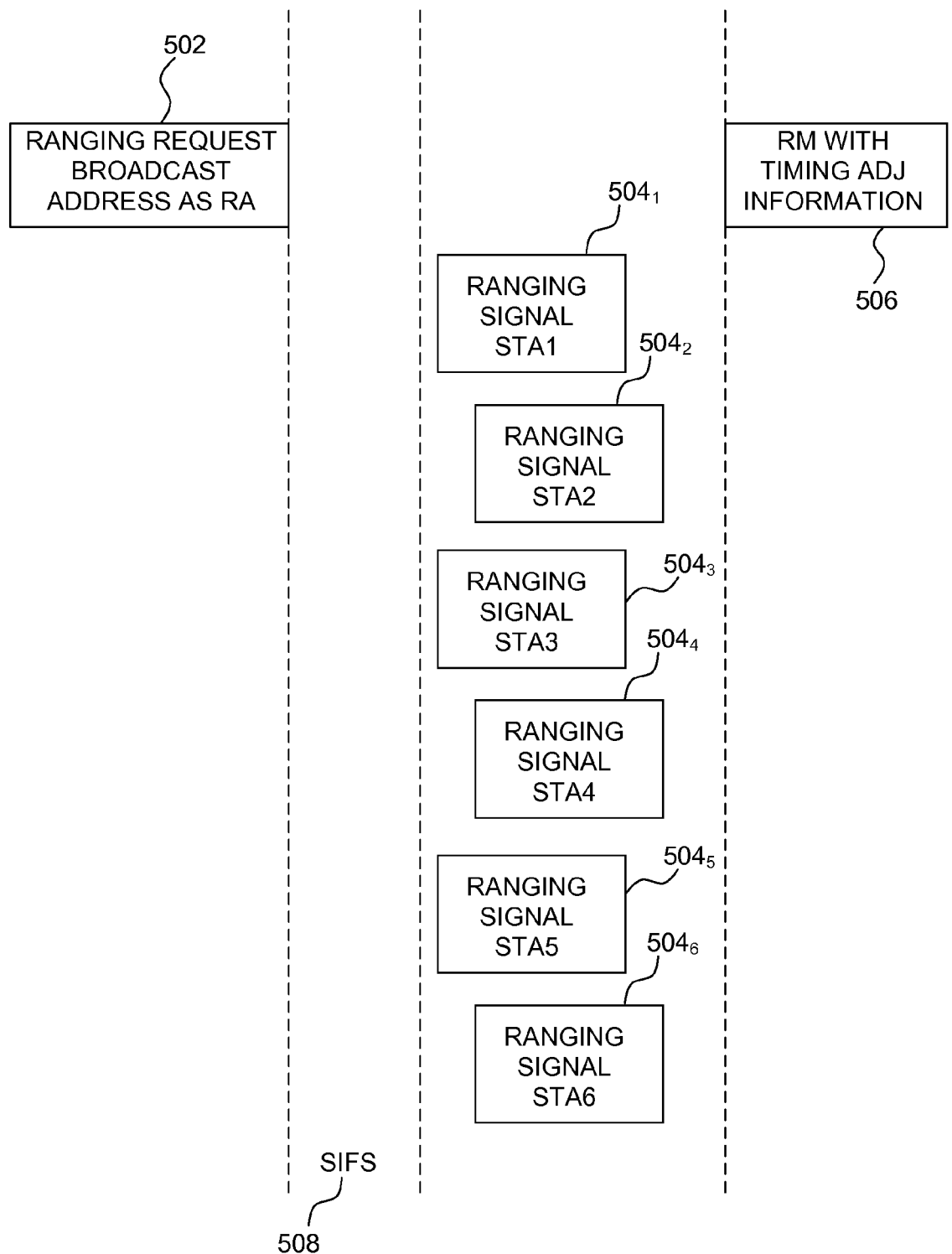
FIG. 5 is a timing diagram illustrating an example of synchronizing a WLAN using ranging signals, according to one embodiment of the disclosure.

The operations of FIG. 4 may be understood with reference to FIG. 5, which shows a timing diagram 400 for an example of ranging for stations in an example system. In a first time slot, the AP sends a ranging request (RNG-REQ) message 502. According to certain aspects, RNG-REQ message 502 may comprise a RNG-REQ message having a format, such as the RNG-REQ described with reference to FIG. 7 below.

As illustrated, the RNG-REQ message 502 may be a multicast message with a Broadcast Address of a Ranging Group ID as a receiver address (RA). For certain embodiments, the STAs may form a ranging group, and each STA may be assigned a Ranging Group ID. The Ranging Group ID may have been assigned to the STA on associate with an AP, for example, during a registration process.

According to certain embodiments, a duration field of the Ranging Request message 502 may be set to cover the transmission time of the ranging signals 504 requested from the stations, which may help accommodate stations that are not SDMA-capable. For example, because stations that are not SDMA-capable, such as legacy stations, will not need to perform the ranging operations described herein, such stations may simply ignore the ranging request and refrain from transmitting for the time indicated by the duration field.

After a fixed duration, such as a short interframe space (SIFS), the stations respond with ranging signals 504. As illustrated, the ranging signals 504 sent by the stations are not time aligned, due to different propagation delays (e.g., due to different distances between the stations and the AP). However, because the AP knows when each station should send its ranging signals 504, relative to receiving the ranging request, it is able to calculate a propagation delay for each station.

For certain embodiments, the stations may send the ranging signals 504 utilizing a CDMA-based scheme. For example, for certain embodiments, each station may select an N-bit Walsh code sequence, divide the sequence into a set of subsequences, and transmit the subsequences as OFDM symbols on a subset of available tones. This may result in efficient ranging transmissions with minimal resource consumption.

Various techniques may be utilized to allow the AP to distinguish the ranging signals sent by each station. For example, for certain embodiments, each station may multiply the selected Walsh code with a complex QPSK scrambling sequence. The scrambling seed used to generate the scrambling sequence may be dependent on the station ID, allowing the AP to distinguish the ranging signals.

Based on the relative propagation delay, the AP may determine timing adjustment information for each station and send the timing adjustment information to each station. As illustrated, the AP may send the timing adjustment information contained in a multicast message, such as any suitable type of request message (RM) 506. According to certain aspects, RM 506 may comprise a training request message (TRM), such as the TRM described with reference to FIG. 6 below. The stations may use the timing adjust information from the ranging procedure to adjust the start time of various SDMA uplink (UL) transmissions (such as sounding messages, block ACKs, and SDMA data transmissions), so their arrival is synchronized with the arrival of transmissions from other stations, allowing the AP to effectively decode the SDMA transmissions. For certain embodiments, in addition to initial ranging operations, the AP may also provide timing adjustments as feedback, based on received UL transmissions.

For certain embodiments, the AP may send, as timing adjust information (e.g., sent in an RM 506 with timing information as shown in FIG. 5), a relative delay each station may use to adjust the start time of SDMA UL transmissions. For example, stations with the greatest propagation delay (e.g., those farthest from the AP), may have the smallest (or no) timing adjustment, so its transmissions are sent earlier than other stations to compensate for the greater propagation delay. Stations with smaller propagations delay (relative to the maximum) may adjust their timing by delaying the start of their SDMA UL transmissions.

This algorithm may be illustrated by a simple example assuming four stations STA1-STA4. After receiving ranging signals from the four stations, the AP may determine STA4 has the maximum propagation delay (maxD). This maximum propagation delay may be used to adjust the timing of all stations based on their corresponding propagation delay. For example, assuming stations STA1, STA2, and STA3, have propagation delays $D_{a1}$, $D_{a2}$, and $D_{a3}$, the AP may calculate their timing adjustments, such that their transmissions are delayed as follows:

STA1 transmissions may be delayed by max$D$–$D_{a1}$;

STA2 transmissions may be delayed by max$D$–$D_{a2}$;

STA1 transmissions may be delayed by max$D$–$D_{a3}$;

The actual timing adjustment information may be conveyed in any suitable form. For example, for certain embodiments, timing adjustments may be conveyed as an N-bit code that indicates a relative delay in predefined delay increments. For example, assuming a 50 ns delay increment, an N-bit code with a value representing 2 would result in a transmission delay of 100 ns.

How often ranging operations are performed, as well as the actual increment and range of adjustment may be determined based on expected application parameters, such as how fast a station is expected to move. For example, assuming a maximum speed of 10 Km/h (approx. 8.3 ft/s), even with two nodes going in opposite directions, the resulting relative speed would be approximately 16.6 ft/s. The approximate time to travel 50 feet (corresponding to a change of approximately 50 ns in propagation delay) at this speed is 3 seconds. Thus, in this relatively extreme scenario, performing ranging operations every 3 seconds would likely be sufficient to keep stations synchronized. In more normal scenarios, performing ranging operations once every 10 seconds would likely be more than sufficient. Regarding the delay range, assuming a range requirement of 300 feet (100 m), a propagation delay of 1 ns per foot, and a sampling duration of 50 ns, the maximum delay (corresponding to 300 ns) would be 6 samples. Thus, a maximum of 3 bits to represent timing adjustment information would be sufficient in this scenario.

Figure 6:
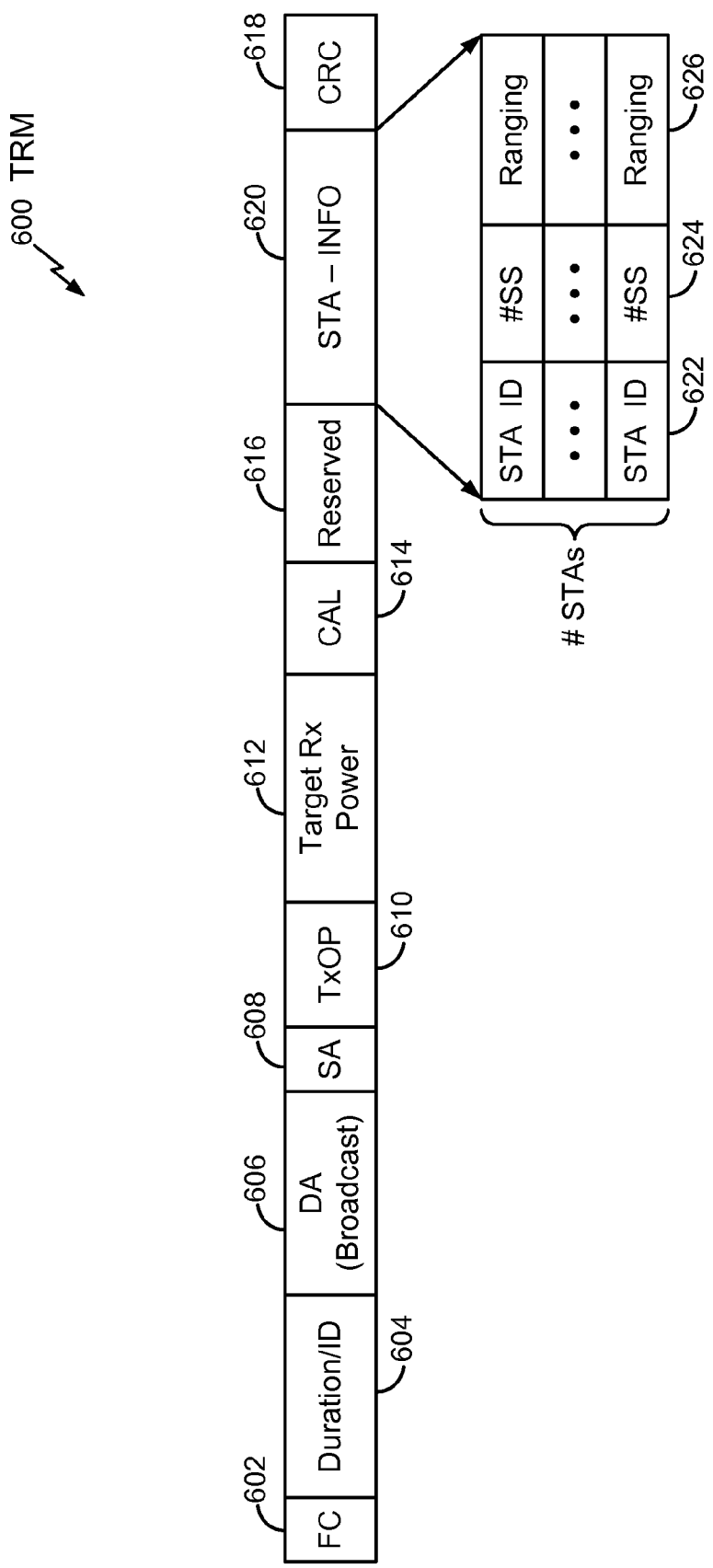
FIG. 6 illustrates an example format of a training request message (TRM), according to one embodiment of the disclosure.

FIG. 6 illustrates an example format of a training request message (TRM) 600 that the AP may use to convey timing adjustment information for certain embodiments of the present disclosure. According to certain embodiments, the TRM 600 may include a frame control (FC) field 602. The FC field 602 may include some number of bits (e.g., 16 bits) with various information, such as a Protocol version, frame type and subtype.

The TRM 600 may also include a Duration/ID field 604 indicating how long the related transmission will be used. The Duration/ID field 604 may include, for example, 16 bits, which may be set to cover subsequent transmissions (e.g., additional training or acknowledgements).

The TRM 600 may also include a recipient or destination address (DA) 606 source address (SA) 608, which may both be 48-bit addresses, for example. The DA 606 may be set to multicast/broadcast address for a set of stations receiving the information. The SA 608 may be set to an address of the AP sending the TRM. A transmit opportunity (TxOP) field 610 may indicate (e.g., with 10 bits) an amount of time allocated for acknowledgement of the TRM 600. A target receive (Rx) power field 612 may provide an indication of a reference receive power (e.g., as a 6-bit number). A receiving station may compare the actual receive power of the TRM (as received at the station) to the target Rx power field to obtain an indication of proximity of the station to the AP and may adjust its transmission power accordingly. A calibration (CAL) position field 614 may have one or more bits set to indicate occurence/non-occurence of a calibration procedure. According to some embodiments, a set of reserved bits 616 (e.g., 7 bits) may be reserved to accommodate future functionality. A CRC field 618 (e.g., 32-bits) may allow for error correction.

The TRM 600 may also include a station information field 620 that may include information for the group of stations. As illustrated, for some embodiments, the station information field 620 may include information for a number of stations. Because the number of stations may vary, the size of the station information field 620 may vary. For each station, a station id (STA ID) field 622, a field 624 indicating a number of spatial streams (#SS) allocated to a station, and a ranging field 626. The STA ID field 622 may include an identification (e.g., a 16-bit ID) of a station, while the #SS field 624 may indicate a number of spatial streams (e.g., as a 4 bit number) allocated to the identified station, while the ranging field 626 may specify a number of time increments (e.g., 4 bits) to advance or retard transmission timing so SDMA transmissions from different stations arrive at the AP nearly simultaneously.

For certain embodiments, a TRM message may only require a subset of the illustrated fields as mandatory fields. For example, for certain embodiments, only the FC field 602, Duration/ID field 604, DA field 606, SA field 608, STA INFO field 620, and CRC 618 may be mandatory. Further, for certain embodiments, rather than include ranging information for a plurality of stations in the STA INFO field 620, while less efficient, separate messages may be sent for each station.

Figure 7:
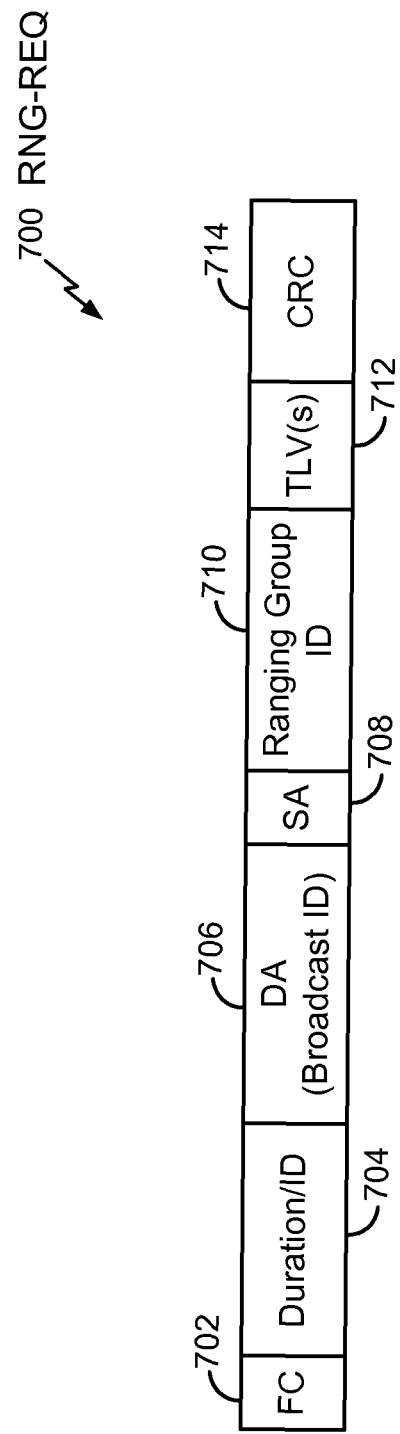
FIG. 7 illustrates an example format of a ranging request (RNG-REQ) message, according to one embodiment of the disclosure.

FIG. 7 illustrates an example format of a ranging request (RNG-REQ message) 700 that the AP may send to prompt the stations to send ranging signatures for certain embodiments of the present disclosure. As with the TRM 600 described above, the RNG-REQ message may also include an FC field 702, Duration/ID field 704, DA field 706, SA field 708, and CRC field 714, which may be used as described above with reference to the TRM 600.

In general, the RNG-REQ message may utilize a legacy message format, but may also include a ranging group ID field 710. This field may be (e.g., 16 bits) and may identify a ranging group ID for a set of stations. The duration/ID field 704 may be set to cover the subsequent training (e.g., sounding and CQI) frames. The RNG-REQ message 700 may also include one or more type length variable (TLV) fields 712 that may be used to convey a variety of information.

For certain embodiments, a RNG-REQ message may only require a subset of the illustrated fields as mandatory fields. For example, for certain embodiments, at least the DA field 706 and the Ranging Group ID field 710 may be mandatory. However, according to certain embodiments, use of the Ranging Group ID field 710 may unambiguously identify the targeted stations and, thus, eliminate the need to use a DA field 706.

Figure 4A:
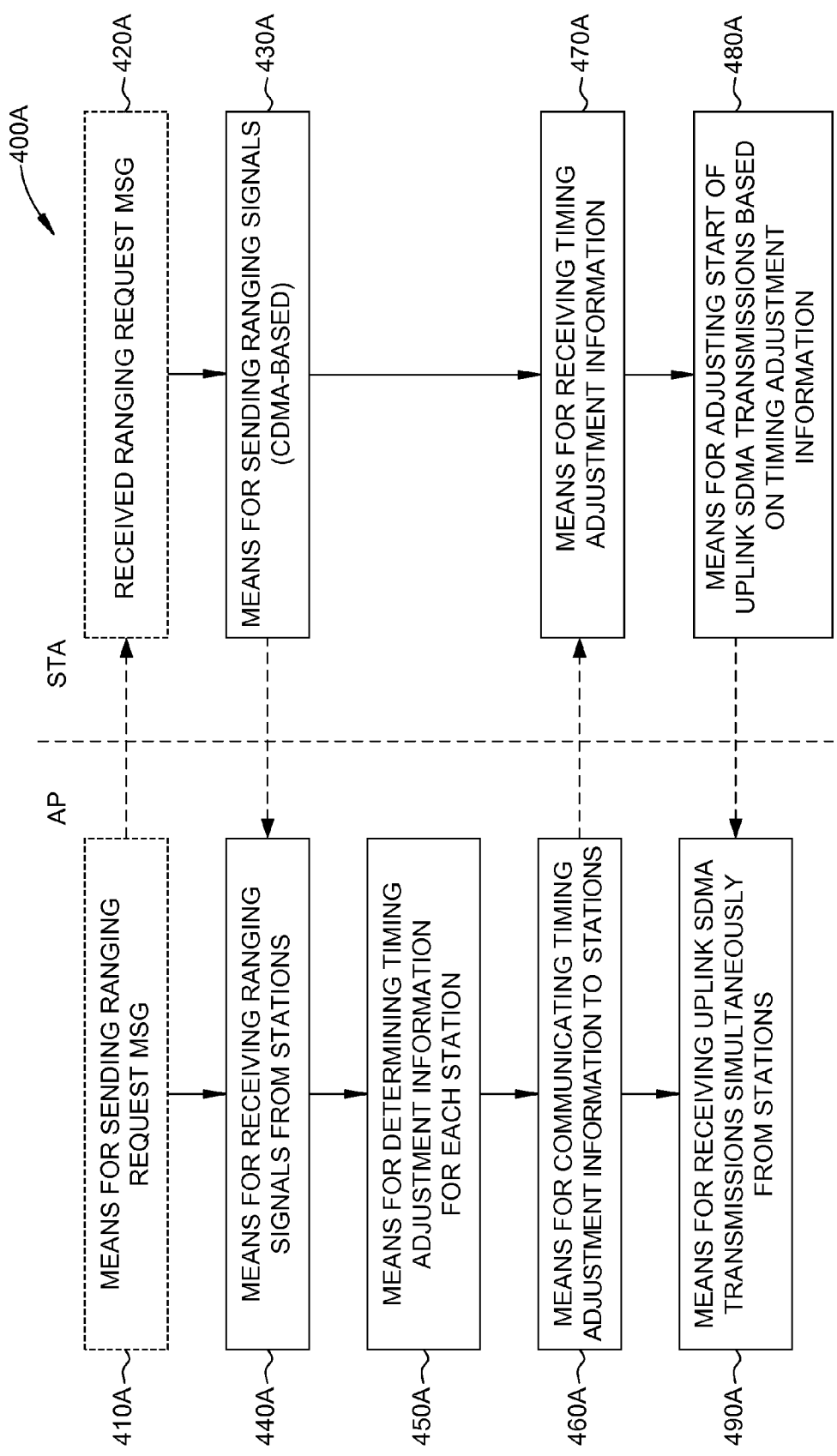
FIG. 4A illustrates example components capable of performing the operations shown in FIG. 4.

The various operations of methods described above may be performed by logic implemented in various hardware and/or software component(s) and/or module(s) corresponding to means-plus-function blocks illustrated in the figures. Generally, where there are methods illustrated in figures any suitable means having corresponding counterpart means-plus-function figures, the operation blocks correspond to means-plus-function blocks with similar numbering. For example, operations 400 shown in FIG. 4 may be performed by corresponding means 400A shown in FIG. 4A.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

Information and signals may be represented using any of a variety of different technologies and techniques. For example, data, instructions, commands, information, signals and the like that may be referenced throughout the above description may be represented by voltages, currents, electromagnetic waves, magnetic fields or particles, optical fields or particles or any combination thereof.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the present disclosure may be embodied directly in hardware, in a software module executed by a processor, or in a combination of the two. A software module may reside in any form of storage medium that is known in the art. Some examples of storage media that may be used include random access memory (RAM), read only memory (ROM), flash memory, EPROM memory, EEPROM memory, registers, a hard disk, a removable disk, a CD-ROM and so forth. A software module may comprise a single instruction, or many instructions, and may be distributed over several different code segments, among different programs, and across multiple storage media. A storage medium may be coupled to a processor such that the processor can read information from, and write information to, the storage medium. In the alternative, the storage medium may be integral to the processor.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware or any combination thereof. If implemented in software, the functions may be stored as one or more instructions on a computer-readable medium. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray® disc where disks usually reproduce data magnetically, while discs reproduce data optically with lasers.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

What is claimed is:

1. A method for adjusting the timing of packet transmissions in a wireless communications system, comprising:
   receiving ranging signals from a plurality of wireless network nodes;
   determining timing adjustment information for adjusting starting timing of packet transmissions from the wireless network nodes based on the ranging signals, wherein determining the timing adjustment information comprises:
   calculating a propagation delay for each node;
   determining a maximum propagation delay from the calculated propagation delays; and
   determining a timing adjustment for each node based on the propagation delay for each node and the maximum propagation delay; and
   communicating the timing adjustment information to the wireless network nodes.

2. The method of claim 1, further comprising:
   sending a ranging request message to the wireless network nodes; and
   wherein the ranging signals are received in response to the ranging request message.

3. The method of claim 2, wherein:
   the plurality of wireless network nodes belong to a ranging group; and
   the ranging request message includes, as a destination address, an identification corresponding to the ranging group.

4. The method of claim 1, wherein ranging signals are transmitted from the wireless network nodes using a code division multiple access (CDMA) transmission scheme.

5. The method of claim 1, wherein communicating the timing adjustment information to the wireless network nodes comprises:
   transmitting one or more request messages (RMs) containing the timing adjustment information.

6. The method of claim 5, wherein transmitting one or more request messages (RMs) containing the timing adjustment information comprises:

transmitting a request message (RM) having a broadcast address of the plurality of wireless nodes; and the request message contains timing adjustment information for the plurality of wireless nodes.

7. The method of claim 1, further comprising:

repeating the receiving, determining, and communicating to update the timing adjustment information for the wireless nodes.

8. A method for adjusting the timing of packet transmissions in a wireless communications system, comprising:

receiving timing adjustment information that is determined by: calculating a propagation delay for each node of multiple wireless nodes, determining a maximum propagation delay from the calculated propagation delays, and determining a timing adjustment for each node based on the propagation delay for each node and the maximum propagation delay; and utilizing the timing adjustment information to adjust the timing of transmitting packets on an uplink connection used by the multiple wireless nodes to simultaneously transmit packets via a multiple access (MA) scheme.

9. The method of claim 8, further comprising:

transmitting ranging signals; and wherein the received timing adjustment information is calculated based, at least in part, on the transmitted ranging signals.

10. The method of claim 9, further comprising:

receiving a ranging request message; and transmitting the ranging signals in response to the ranging request message.

11. The method of claim 8, wherein the multiple access scheme comprises spatial division multiple access (SDMA).

12. An apparatus for adjusting the timing of packet transmissions in a wireless communications system, comprising:

logic for receiving ranging signals from a plurality of wireless network nodes;

logic for determining timing adjustment information for adjusting starting timing of packet transmissions from the wireless network nodes based on the ranging signals, wherein the logic for determining the timing adjustment information comprises:

logic for calculating a propagation delay for each node;

logic for determining a maximum propagation delay from the calculated propagation delays; and logic for determining a timing adjustment for each node based on the propagation delay for each node and the maximum propagation delay; and logic for communicating the timing adjustment information to the wireless network nodes.

13. The apparatus of claim 12, further comprising:

logic for sending a ranging request message to the wireless network nodes; and wherein the ranging signals are sent from the plurality of wireless nodes in response to the ranging request message.

14. The apparatus of claim 12, wherein:

the plurality of wireless network nodes belong to a ranging group; and the ranging request message includes, as a destination address, an identification corresponding to the ranging group.

15. The apparatus of claim 12, wherein ranging signals are transmitted from the wireless network nodes using a code division multiple access (CDMA) transmission scheme.

16. The apparatus of claim 12, wherein communicating the timing adjustment information to the wireless network nodes comprises:

logic for transmitting one or more request messages (RMs) containing the timing adjustment information.

17. The apparatus of claim 16, wherein transmitting one or more request messages (RMs) containing the timing adjustment information comprises:

logic for transmitting a request message (RM) having a broadcast address of the plurality of wireless nodes and containing timing adjustment information for the plurality of wireless nodes.

18. The apparatus of claim 12, wherein the logic for communicating the timing adjustment information to the wireless network nodes periodically communicates updates timing adjustment information for the wireless nodes.

19. An apparatus for adjusting the timing of packet transmissions in a wireless communications system, comprising:

logic for receiving timing adjustment information, wherein the timing adjustment information is determined by: calculating a propagation delay for each node of multiple wireless nodes, determining a maximum propagation delay from the calculated propagation delays, and determining a timing adjustment for each node based on the propagation delay for each node and the maximum propagation delay; and logic for utilizing the timing adjustment information to adjust the timing of transmitting packets on an uplink connection used by the multiple wireless nodes to simultaneously transmit packets via a multiple access (MA) scheme.

20. The apparatus of claim 19, further comprising:

logic for transmitting ranging signals; and wherein the received timing adjustment information is calculated based, at least in part, on the transmitted ranging signals.

21. The apparatus of claim 20, further comprising:

logic for receiving a ranging request message; and logic for transmitting the ranging signals in response to the ranging request message.

22. The apparatus of claim 19, wherein the multiple access scheme comprises spatial division multiple access (SDMA).

23. An apparatus for adjusting the timing of packet transmissions in a wireless communications system, comprising:

means for receiving ranging signals from a plurality of wireless network nodes;

means for determining timing adjustment information for adjusting starting timing of packet transmissions from the wireless network nodes based on the ranging signals, wherein the means for determining the timing adjustment information comprises:

means for calculating a propagation delay for each node;

means for determining a maximum propagation delay from the calculated propagation delays; and means for determining a timing adjustment for each node based on the propagation delay for each node and the maximum propagation delay; and means for communicating the timing adjustment information to the wireless network nodes.

24. The apparatus of claim 23, further comprising:

means for sending a ranging request message to the wireless network nodes; and wherein the ranging signals are sent from the plurality of wireless nodes in response to the ranging request message.

25. The apparatus of claim 24, wherein:

the plurality of wireless network nodes belong to a ranging group; and the ranging request message includes, as a destination address, an identification corresponding to the ranging group.

26. The apparatus of claim 23, wherein ranging signals are transmitted from the wireless network nodes using a code division multiple access (CDMA) transmission scheme.

27. The apparatus of claim 23, wherein the means for communicating the timing adjustment information to the wireless network nodes comprises:
    means for transmitting one or more request messages (RMs) containing the timing adjustment information.

28. The apparatus of claim 27, wherein the means for transmitting one or more request messages (RMs) containing the timing adjustment information comprises:
    means for transmitting a request message (RM) having a broadcast address of the plurality of wireless nodes and containing timing adjustment information for the plurality of wireless nodes.

29. The apparatus of claim 23, wherein the means for communicating the timing adjustment information to the wireless network nodes periodically communicates updates timing adjustment information for the wireless nodes.

30. An apparatus for adjusting the timing of packet transmissions in a wireless communications system, comprising:
    means for receiving timing adjustment information, wherein the timing adjustment information is determined by: calculating a propagation delay for each node of multiple wireless nodes, determining a maximum propagation delay from the calculated propagation delays, and determining a timing adjustment for each node based on the propagation delay for each node and the maximum propagation delay; and
    means for utilizing the timing adjustment information to adjust the timing of transmitting packets on an uplink connection used by the multiple wireless nodes to simultaneously transmit packets via a multiple access (MA) scheme.

31. The apparatus of claim 30, further comprising:
    means for transmitting ranging signals; and
    wherein the received timing adjustment information is calculated based, at least in part, on the transmitted ranging signals.

32. The apparatus of claim 31, further comprising:
    means for receiving a ranging request message; and
    means for transmitting the ranging signals in response to the ranging request message.

33. The apparatus of claim 30, wherein the multiple access scheme comprises spatial division multiple access (SDMA).

34. A computer-program product for adjusting the timing of packet transmissions in a wireless communications system comprising a non-transitory computer readable medium having instructions stored thereon, the instructions being executable by one or more processors and the instructions comprising instructions for:
    receiving ranging signals from a plurality of wireless network nodes;
    determining timing adjustment information for adjusting starting timing of packet transmissions from the wireless network nodes based on the ranging signals, wherein determining the timing adjustment information for comprises:
        calculating a propagation delay for each node;
        determining a maximum propagation delay from the calculated propagation delays; and
        determining a timing adjustment for each node based on the propagation delay for each node and the maximum propagation delay; and
    communicating the timing adjustment information to the wireless network nodes.

35. A computer-program product for adjusting the timing of packet transmissions in a wireless communications system comprising a non-transitory computer readable medium having instructions stored thereon, the instructions being executable by one or more processors and the instructions comprising instructions for:
    receiving timing adjustment information that is determined by: calculating a propagation delay for each node of multiple wireless nodes, determining a maximum propagation delay from the calculated propagation delays, and determining a timing adjustment for each node based on the propagation delay for each node and the maximum propagation delay; and
    utilizing the timing adjustment information to adjust the timing of transmitting packets on an uplink connection used by the multiple wireless nodes to simultaneously transmit packets via a multiple access (MA) scheme.

* * * * *